US010975347B2

(12) United States Patent
Cheyrou et al.

(10) Patent No.: US 10,975,347 B2
(45) Date of Patent: Apr. 13, 2021

(54) FERMENTER FOR A LIQUID MEDIUM WITH GAS CIRCULATION STIRRING, COMPRISING AN AUTOMATIC DEVICE FOR ESTABLISHING A FLUID COMMUNICATION BETWEEN THE ASCENDING CIRCULATION AND THE DESCENDING CIRCULATION VOLUMES DEPENDING ON THE HEIGHT OF THE MEDIUM

(71) Applicant: GG CORIOLIS, Planguenoual (FR)

(72) Inventors: Lagreze Arnaud Cheyrou, Pleneuf Val Andre (FR); Philippe Baillon, Landivisiau (FR); Stephane Fay, Pleneuf Val Andre (FR)

(73) Assignee: BIOREA, Lamballe-Armor (FR)

( * ) Notice: Subject to any disclaimer, the term of this patent is extended or adjusted under 35 U.S.C. 154(b) by 249 days.

(21) Appl. No.: 15/770,416

(22) PCT Filed: Oct. 14, 2016

(86) PCT No.: PCT/FR2016/052659
§ 371 (c)(1),
(2) Date: Apr. 23, 2018

(87) PCT Pub. No.: WO2017/068265
PCT Pub. Date: Apr. 27, 2017

(65) Prior Publication Data
US 2018/0305653 A1 Oct. 25, 2018

(30) Foreign Application Priority Data
Oct. 23, 2015 (FR) ...................... 15/60152

(51) Int. Cl.
*C12M 1/08* (2006.01)
*C12M 1/00* (2006.01)
*C12M 1/06* (2006.01)

(52) U.S. Cl.
CPC ............ *C12M 27/24* (2013.01); *C12M 27/02* (2013.01); *C12M 27/22* (2013.01); *C12M 29/08* (2013.01)

(58) Field of Classification Search
CPC ..................................... C12M 27/24
(Continued)

(56) References Cited

U.S. PATENT DOCUMENTS 3,236,744 A 2/1966 Yamaha et al.
3,539,158 A * 11/1970 Roos ...................... C02F 3/165
261/36.1

(Continued)

FOREIGN PATENT DOCUMENTS

| CH | 489609 A | 4/1970 |
| CN | 1175635 A | 3/1998 |
| CN | 102732416 A | 10/2012 |

OTHER PUBLICATIONS

English Machine Translation to Abstract of CN102732416.
(Continued)

*Primary Examiner* — Holly Kipouros
(74) *Attorney, Agent, or Firm* — Cantor Colburn LLP

(57) ABSTRACT

The invention relates to a digester for a liquid medium, comprising a container, a dividing wall between two spaces, and a device for injecting gas into the lower part of one of the spaces. The gas creates an upflow of the mixture of liquid medium and injected gas in said space, and a downflow in the other space. The dividing wall is equipped with at least one device for establishing a fluid communication between the spaces, so that the fluid communication configuration is
(Continued)

automatically varied between a first open configuration in which fluid can flow freely from one space to the other, and a second closed configuration in which the flow of fluid is blocked fully or partially by the aforementioned device.

34 Claims, 5 Drawing Sheets

(58) Field of Classification Search
USPC .................................................. 435/295.1
See application file for complete search history.

(56) References Cited

U.S. PATENT DOCUMENTS

| | | | | |
|---|---|---|---|---|
| 3,635,796 | A | * | 1/1972 | Imada .................... C12M 27/08 435/3 |
| 5,755,976 | A | * | 5/1998 | Kortmann ........... B01F 3/04517 210/137 |
| 2006/0019379 | A1 | * | 1/2006 | Taylor .................... C12M 47/06 435/306.1 |
| 2014/0065687 | A1 | | 3/2014 | Ericsson |

OTHER PUBLICATIONS

English Machine Translation to Abstract of CN1175635.
International Search Report for Application No. PCT/FR2016/052659.

* cited by examiner

FERMENTER FOR A LIQUID MEDIUM WITH GAS CIRCULATION STIRRING, COMPRISING AN AUTOMATIC DEVICE FOR ESTABLISHING A FLUID COMMUNICATION BETWEEN THE ASCENDING CIRCULATION AND THE DESCENDING CIRCULATION VOLUMES DEPENDING ON THE HEIGHT OF THE MEDIUM

CROSS REFERENCE TO RELATED APPLICATIONS

This application is a National Stage of PCT Application No. PCT/FR2016/052659 filed on Oct. 14, 2016, which claims priority to French Patent Application No. 15/60152 filed on Oct. 23, 2015, the contents each of which are incorporated herein by reference thereto.

TECHNICAL FIELD

The present invention concerns a fermenter for liquid medium for continuous or discontinuous production, comprising stirring means by gas circulation, the fermenter comprising:
- a container adapted to contain the liquid medium,
- a partition wall positioned in the container and separating first and second volumes,
- a device for injecting this gas into the lower part of one of the first or second volumes in order to create in this volume an ascending circulation of the mixture between the liquid medium and the injected gas and a descending circulation of this mixture in the volume not supplied with gas by the injection device.

BACKGROUND

It is known that a fermenter is an apparatus in which a fermentation of the liquid medium is carried out. This device, also known as bioreactor or propagator, allows multiplying microorganisms (yeasts, bacteria, microscopic fungi, algae, animal and plant cells). It allows monitoring the culture conditions such as temperature, pH or gasification, providing a high reliability of the collected information.

Two categories of solutions exist conventionally for stirring the liquid medium during the fermentation process.

The first category of solutions for stirring the liquid medium, which is the most commonly used one, uses motorized means that impose a circulation of the liquid medium, for example with one or several motor(s), particularly via mechanized stirrers.

This solution has the advantage of being able to operate at various levels of liquid medium inside the container. In case of foaming or uncontrolled evaporation of the liquid medium, the latter is still stirred, allowing to avoid a cessation or a significant decrease in gas exchanges. But this solution has yet the disadvantage of being complex and expensive. It requires using motorized systems and closing means associated with the shafts of these motors, which implies the addition of parts, and requires human intervention.

A second category of solutions for stirring the liquid medium provides the use of stirring means by circulating a gas injected into the lower part of the liquid medium, this technology being conventionally known under the terminology "air lift". The invention that will be described concerns a solution falling within this second category.

This solution has the advantage of not using a mechanical system as previously described. But this solution generally requires a constant-level operation of the liquid medium in the container. The foam and the evaporation phenomena are therefore very problematic because, in case of drop in the level of the liquid medium in the container, there is a risk of poor descending circulation and the gasification is no longer effective in a large part of the fermenter. The stirring and the gas exchanges will decrease dramatically in this part of the fermenter. The micro-organisms could die and sediment.

Conventionally, an "air lift" technology fermenter comprises a container containing the liquid medium and at least one partition wall, for example constituted in an inner tube, positioned in the container in order to delimit on either side thereof a first volume and a second volume. A device for injecting gas is arranged in the lower part of one of these two volumes in order to create an ascending circulation of the mixture between the liquid medium and the gas injected into this volume and a descending circulation of this mixture in the volume not supplied with gas by the injection device.

Whatever the height of the inner tube, the system is likely to be deactivated as soon as the liquid medium is in static equilibrium at a given level located below the discharge area.

In order to limit as much as possible the risks of deactivation of the circulation in the fermenter in case of a decrease in the level of liquid medium, in particular in case of foaming or uncontrolled evaporation, there are solutions where the inner tube comprises openings and means for closing these openings controlled manually, just like the solution described in the document U.S. Pat. No. 3,236,744A1. But this solution relies on the human factor and is not reliable. It would also be possible to provide an inner tube having a variable height depending on the level of the liquid medium but this solution would not be easily achievable.

BRIEF SUMMARY

The present invention aims to solve all or part of the drawbacks listed hereinabove.

In this context, there is a need to provide a fermenter for a liquid medium with gas circulation stirring, in other words which corresponds to the second category of solutions mentioned above, which allows:
- being simple, reliable and cost-effective,
- avoiding the risks of external contamination, in particular inherent to the closing means of the axis or actuator passages coming from the outside of the fermenter,
- ensuring a stirring and gas exchanges whatever the level of the liquid medium,
- avoiding the risks of dysfunction of the fermenter and sedimentation of the micro-organisms,
- avoiding the use of motorized systems and limiting the human interventions,
- reducing the use of opening/closing means and of closing means.

These objects can be achieved by a fermenter according to the appended claims.

Particularly, in order to address the issues listed above, a fermenter for a liquid medium is provided, comprising stirring means by gas circulation, comprising a container adapted to contain the liquid medium, a partition wall positioned in the container and separating first and second volumes, a device for injecting said gas into the lower part of one of the first or second volumes in order to create in said volume an ascending circulation of the mixture between the liquid medium and the injected gas and a descending circulation of said mixture in the volume not supplied with gas by said injection device, the partition wall being equipped with at least one device for establishing a fluid communication between the first and second volumes, configured to automatically switch between:

a first configuration wherein the fluid communication device allows, for the liquid medium and the gas contained in the container, a free fluid circulation from one volume to the other through said fluid communication device, the first configuration being assumed as soon as, at the fluid communication device, the difference between the pressure of said mixture in the volume where the ascending circulation occurs and the pressure of said mixture in the volume where the descending circulation occurs is greater than a predetermined threshold value, and a second configuration wherein the fluid communication device blocks all or part of said fluid circulation for the liquid medium and the gas contained in the container, the second configuration being assumed as soon as, at the fluid communication device, the difference between the pressure of said mixture in the volume where the ascending circulation occurs and the pressure of said mixture in the volume where the descending circulation occurs is less than or equal to the predetermined threshold value.

BRIEF DESCRIPTION OF THE DRAWINGS

The invention will be better understood using the following description of particular embodiments of the invention given by way of non-restrictive examples and shown in the appended drawings, wherein.

DETAILED DESCRIPTION

Figure 1:
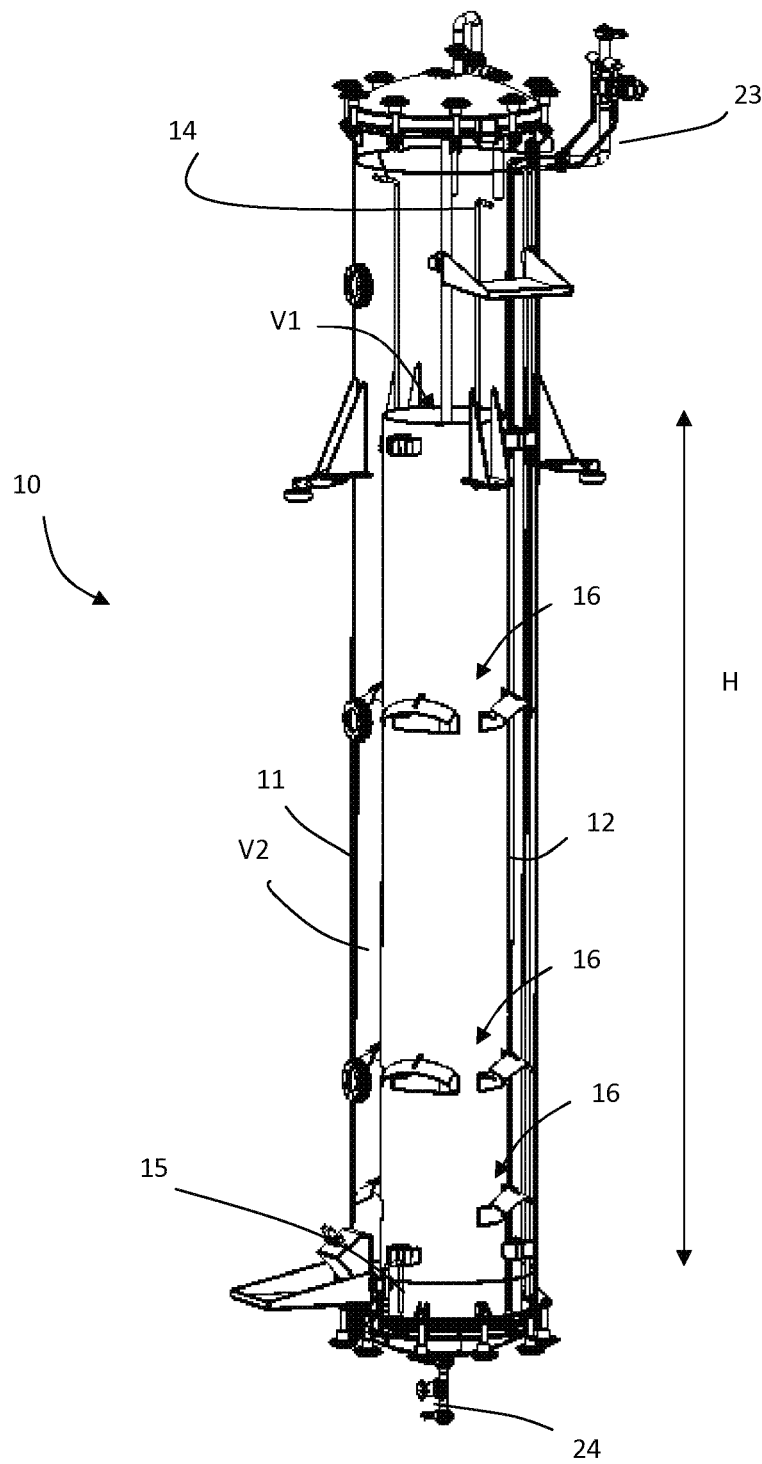
FIG. 1 is a perspective transparent view, of an example of a fermenter according to the invention.

With reference to the appended figures as summarily presented hereinabove, the invention essentially concerns a fermenter 10 for a liquid medium ensuring a continuous or discontinuous production. The fermenter comprises means ensuring a stirring of the liquid medium by gas circulation in the liquid medium. The liquid medium may be a sterile medium or a medium with monitored contamination. The fermenter 10 is therefore of the type corresponding to the "air lift" technology.

The fermenter 10 is generally configured so as to ensure a fermentation of the liquid medium. This apparatus, also known as bioreactor or propagator, allows multiplying microorganisms (yeasts, bacteria, microscopic fungi, algae, animal and plant cells). It allows monitoring the culture conditions such as temperature, pH, gasification or gas exchanges, thereby providing a high reliability of the collected information.

In general, the fermenter 10 which will be described in detail hereinbelow comprises:
a container 11 adapted to contain the liquid medium, being of any shape,
a partition wall positioned in the container 11 and separating the first and second volumes V1, V2 inside the container 11,
a gas injection device 13 mentioned above configured to inject the gas into the lower part of the first volume V1 or of the second volume V2 in order to create, in this volume where the injection occurs, an ascending circulation of the mixture between the liquid medium and the injected gas, and a descending circulation of this mixture in the other volume, that is to say in the volume not supplied with gas by the injection device 13.

The partition wall, which has a height marked H, may be of any nature, constitution or shape. In the illustrated example, the partition wall is formed in an inner tube 12 positioned in the container 11 so that the inner tube 12 internally delimits the first volume V1 and externally delimits the second volume V2 in combination with the container 11. In other words, in this particular example, the first volume V1 corresponds to the inner volume delimited by the inner tube 12 while the second volume V2 is located around the inner tube 12, between the latter and the walls of the container 11.

But it goes without saying that this construction of the partition wall in the form of a single inner tube 12 is not restrictive. In particular, it is for example possible to provide for several concentric tubes having sections of any shape, or parallel compartments in a container 11 of any shape, for example rectangular shape.

In the shown variant and in a non-restrictive manner, the injection device 13 injects the gas into the lower part of the first volume V1, so that the ascending circulation of the mixture between the liquid medium and the injected gas occurs in the first volume V1, that is to say inside of the inner tube 12, herein of circular section. The descending circulation of this mixture then occurs in the second volume V2, that is to say in the intermediate volume, here of annular section, between the inner wall of the container 11 and the outer wall of the inner tube 12.

However, it is quite possible to consider an inverted configuration wherein the injection device 13 would inject the gas into the lower part of the second volume V2 so that the ascending circulation of the mixture between the liquid medium and the injected gas occurs in the second volume V2 comprised between the container 11 and the inner tube 12. In this alternative, the descending circulation then occurs in the first volume V1, inside the inner tube 12.

In the figures, the container 11 of the fermenter 10 comprises an inlet 14 for supplying the container 11, and thus the fermenter 10, with a liquid medium to be fermented and an outlet 15 for discharging the liquid medium from the container 11 after fermentation, and thus from of the fermenter 10. The inlet 14 and the outlet 15 can be equipped with all the conventional means known in the concerned technical field, for example allowing to regulate the flow rate of the liquid medium entering the fermenter 10 via the inlet 14 and/or leaving the fermenter 10 from the outlet 15. In general, the fermenter 10 may be equipped with all the means conventionally used in the technical field of the fermenters, in particular any sensor or the same allowing to determine a physical feature of the liquid medium or of the mixture in this area, such as for example the temperature, the pressure, the flow rate, the level, a foam detecting element, etc. The fermenter 10 also comprises an inlet 23 for supplying the gas to the injection device 13 and a drainage system 24.

The partition wall is equipped with at least one fluid communication device 16 selectively allowing or not to put in fluid communication the first and second volumes V1, V2 with each other. Each fluid communication device 16 is in particular configured to switch automatically, without any human intervention for this purpose, between:
- a first configuration (FIG. 6) wherein the fluid communication device 16 allows, for the liquid medium and the gas contained in the container 11, a free fluid circulation from one volume to the other through said fluid communication device 16,
- and a second configuration (FIG. 5) wherein the fluid communication device 16 blocks all or part of this fluid circulation for the liquid medium and the gas contained in the container 11.

Advantageously, said at least one fluid communication device 16 is automatic in a manner requiring no manual intervention, operating autonomously, which allows a reliable and effective circulation and therefore an optimal stirring.

The first configuration is assumed as soon as, at the fluid communication device 16, at least one physical parameter of the mixture satisfies a predetermined condition. The second configuration is assumed as soon as, at the fluid communication device 16, said at least one physical parameter does not satisfy the predetermined condition mentioned above.

Said at least one physical parameter comprises the pressure value of the mixture respectively in the first and second volumes V1 and V2. The first configuration is assumed as soon as, at the fluid communication device 16, the difference between the pressure in the volume where the ascending circulation occurs and the pressure in the volume where the descending circulation occurs is greater than a predetermined threshold value. This situation may occur when the liquid medium in the volume where the ascending circulation occurs no longer communicates with the volume where the descending circulation occurs, due to a difference in level no longer allowing the liquid medium to overflow from the ascending circulation volume to the descending circulation volume. On the contrary, the second configuration is assumed as soon as, at the fluid communication device 16, the difference between the pressure in the volume where the ascending circulation occurs and the pressure in the volume where the descending circulation occurs is less than or equal to the aforementioned predetermined threshold value.

It is clear that the pressure difference between the ascending circulation and the descending circulation volumes may perfectly be induced by a difference in the level of the liquid medium in these two volumes respectively. For example, if the level of the liquid medium in the descending circulation volume is less than the level of the liquid medium in the ascending circulation volume, the pressure differential is reversed relative to the normal state of the fermenter 10 in continuous mode; in fact, the pressure of the liquid medium in the ascending circulation volume becomes greater than the pressure of the liquid medium in the descending circulation volume.

The predetermined threshold value beyond which the first configuration is automatically applied may be equal to 0 (the second configuration being then adopted automatically in case of equal pressure between the volumes V1 and V2 at the device 16) or adopt a constant value greater than 0 and fixed by a suitable mechanical member, such as a spring or the like.

Figure 4A:
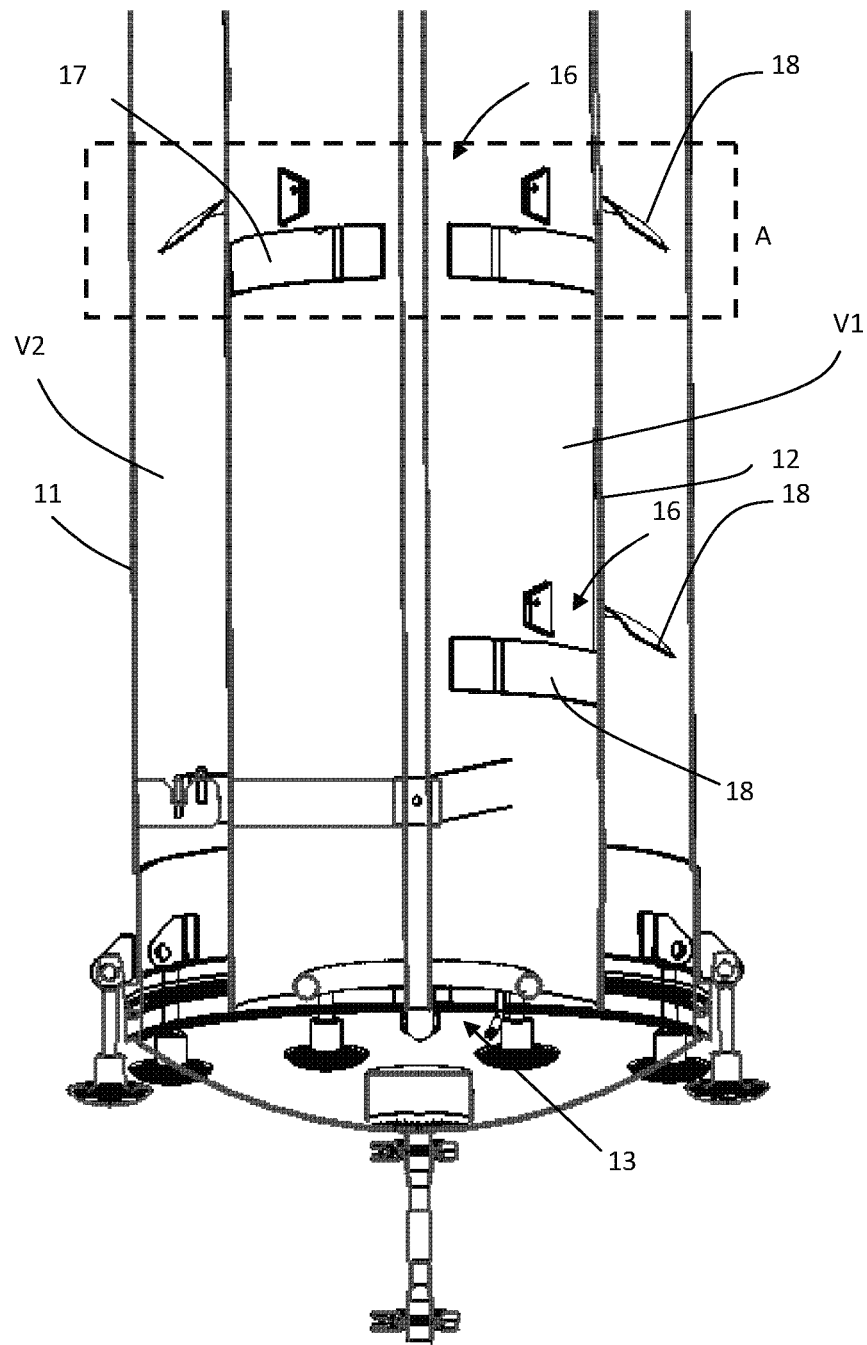
FIG. 4A is a partial perspective and transparent view of the fermenter of FIG. 1, showing a plurality of communication devices, each assuming its first configuration.
Figure 4B:
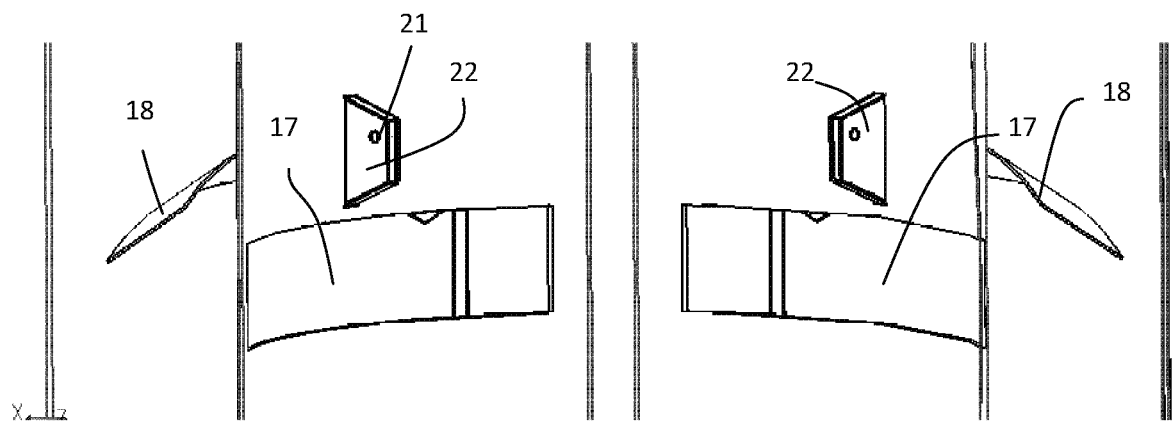
FIG. 4B shows in detail the area marked A in FIG. 4A, And FIGS. 5 and 6 show schematically a fermenter according to the invention, in longitudinal section, respectively in the second configuration and in the first configuration.

FIGS. 1, 4A and 4B show the fermenter 10 in the hypothetical situation where each fluid communication device 16 adopts its first configuration, for understanding reasons only. In use, it goes without saying that each fluid communication device 16 adopts its second configuration when it is not immersed in the liquid medium or when the pressure difference between the two volumes is not sufficient to exceed the threshold value.

Figure 5:
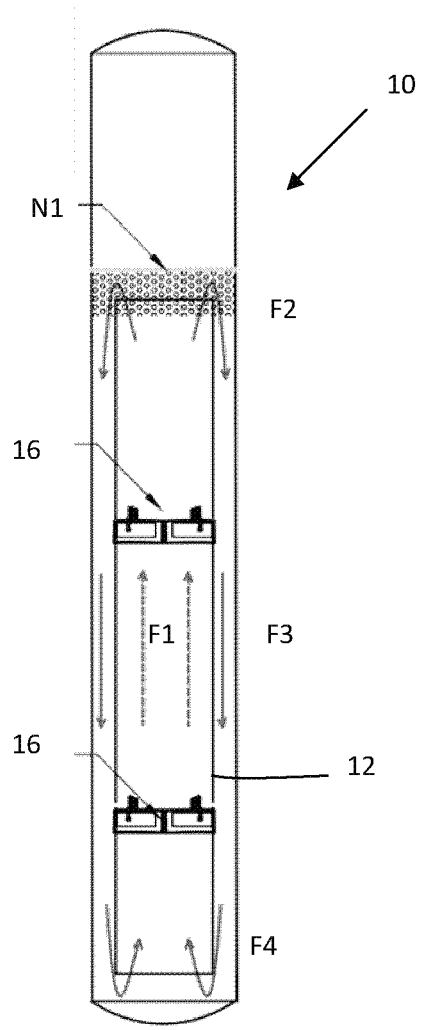
Figure 6:
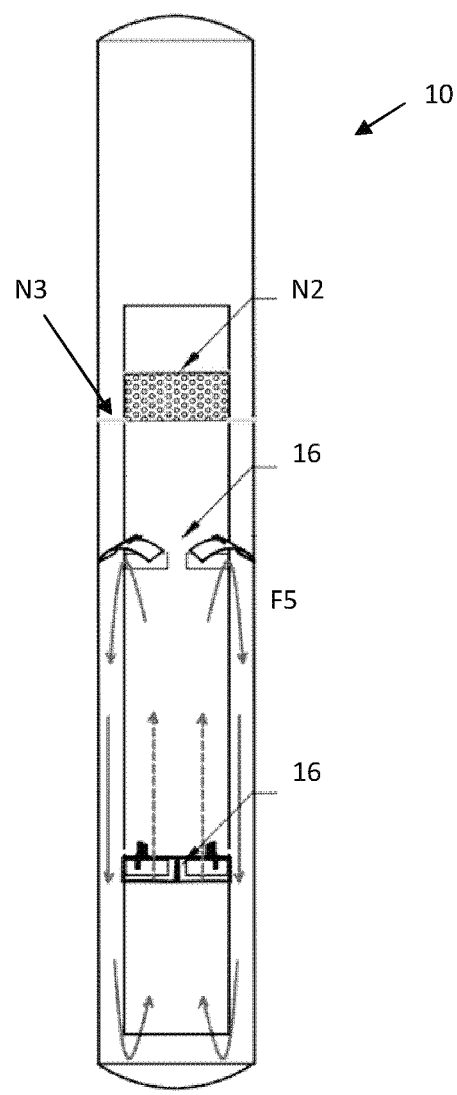

According to a particular embodiment, the fermenter 10 comprises a plurality of separate fluid communication devices 16 arranged in different areas of the partition wall which are staggered along its height H. In other words, the fluid communication devices 16 are arranged in different areas of the inner tube 12 staggered on its height. It is specified that the inner tube 12 is oriented vertically so that its height corresponds to the direction along which the level of liquid medium varies within the container 11. In the particular example illustrated in FIGS. 1, 2, 3, 4a and 4B, the fermenter 10 comprises three separate fluid communication devices 16 staggered along the height of the inner tube 12. In FIGS. 5 and 6, the fermenter 10 comprises only two separate fluid communication devices staggered along the height of the inner tube 12: an upper fluid communication device 16 and a lower fluid communication device 16, are arranged independent of each other. It goes without saying that the fluid communication devices 16 may be of any number, depending for example on the height H of the partition wall, on the required accuracy, on the nature of the liquid medium, etc. The fluid communication devices 16 may be distributed over all or part of the height H of the partition wall, at a regular pitch or not.

In FIG. 6, only the upper fluid communication device 16 assumes its first configuration while, at the same time, the lower fluid communication device 16 is in the second configuration.

In FIG. 5, the upper fluid communication device 16 and the lower fluid communication device 16 are both in their second configurations.

The fermenter 10 allows solving the problems raised by the fermenters of the prior art. In a normal operating situation of the fermenter 10, which is shown in FIG. 5, each fluid communication device 16 is in its second configuration. This is why in FIG. 5, the upper fluid communication device 16 is in its second configuration and the lower fluid communication device 16 is also in its second configuration. Each fluid communication device 16 is therefore normally closed in the normal situation of the fermenter 10 and blocks the circulation from one volume to the other, in particular when the level N1 of liquid medium in the fermenter 10 remains generally constant (the pressures in the volumes V1, V2 on either side of each device being substantially identical). The direction of the ascending circulation in the first volume V1 is indicated by the arrows F1. The direction of the descending circulation inside the second volume V2 is symbolized by the arrows F3. In the upper part of the fermenter 10, from the top of the partition wall, the discharge of the liquid medium from the ascending circulation volume to the descending circulation volume is represented by the arrows F2. In the lower part of the fermenter 10, from below the partition wall, the return of the liquid medium to pass from the descending circulation volume to the ascending circulation volume is shown schematically by the arrows F4.

FIG. 6 shows, however, a situation of the fermenter 10 in which one of the fluid communication devices 16 automatically and autonomously assumes its first configuration. The arrows F1, F3 and F4 are always illustrated to show that in these areas, the way the liquid medium circulates is identical to that of FIG. 5. But in FIG. 6 the arrows F2 are absent because the discharge of the liquid medium does not occur from one volume to the other above the partition wall. On the contrary, when the level of liquid medium tends to drop in the fermenter 10, for example in case of foaming or uncontrolled evaporation, the pressure in the ascending circulation volume (here in the volume V1) tends to increase relative to the pressure in the descending circulation volume (here in volume V2). In FIG. 6, the level of the liquid medium in the fermenter 10 has generally decreased compared to the level N1 initially assumed in the normal situation of FIG. 5: the level of the liquid medium in the ascending circulation volume is noted N2 and the level of liquid medium in the descending circulation volume is noted N3, the levels N2 and N3 being therefore located below the level N1, for example due to uncontrolled evaporation or foaming. On the other hand, because of pressure differences in both volumes, the level N3 is below the level N2. The pressure difference in the volumes V1 and V2 that is concomitant with the difference between levels N2 and N3 in the volumes V1 and V2 can increase until it becomes, at least in some areas of the height H of the partition wall (which corresponds here to the height of the inner tube 12), greater than the predetermined threshold value associated with the pressure differential. In these areas where the threshold value is exceeded, the fluid communication device 16 subject to this pressure differential automatically assumes temporarily the first configuration under the effect of this pressure difference. This is the reason why, in FIG. 6, the upper fluid communication device 16 assumes automatically its first configuration. However, FIG. 6 shows the particular case where the pressure difference in the volumes V1 and V2 is not sufficient to exceed the predetermined threshold value: the lower fluid communication device 16 therefore remains in its second configuration, unlike the upper fluid communication 16 device. The fluid communication devices 16 of the same fermenter 10 are autonomous and independent from each other, each operating automatically without any external action other than the actions of the pressures differentials in the two volumes on either side of the fluid communication devices 16.

In FIG. 6, the switching of the upper fluid communication device 16 to its first configuration promotes a return to the initial pressures (when the level N1 was established) in the two volumes V1, V2. Such a change to the first configuration allows the liquid medium and the injected gas to circulate freely through the upper fluid communication device 16 thus opened, in particular in a direction (schematized by the arrows F5) from the volume where the ascending circulation occurs to the volume where the descending circulation occurs. This temporary, free and automatic circulation of the liquid medium through the upper fluid communication device 16 has the effect of compensating for and correcting the consequences of the drop in the level of the liquid medium in the fermenter 10. Hence, the circulation inside the fermenter 10 does not stop. This allows avoiding a blocking of the fermenter 10 and a risk of a dead area deprived of circulation and gaseous exchange, which would otherwise lead to a cessation of fermentation or even a change in the liquid medium conditions, likely to cause the death of microorganisms. Then, when the level of the liquid medium is increased and the discharge resumes at the top of the partition wall, the pressure in the ascending circulation volume decreases while the pressure in the descending circulation volume increases. The upper fluid communication device 16 then goes back automatically to its second configuration. In the illustrated example, the liquid medium tends to circulate from the first volume V1 to the second volume V2 in the first configuration of each fluid communication device 16. When the level of the liquid medium is allowed to increase sufficiently in the fermenter 10, a low-pressure in the ascending circulation volume and an overpressure in the descending circulation volume are generated again, sufficient to automatically cause the return of the concerned fluid communication device to the second configuration.

The arrangement of several fluid communication devices 16 at different heights has the advantage of automatically and autonomously compensating for the variations in the height of the liquid medium, especially in a situation of foaming and uncontrolled evaporation, and of limiting the risks of blocking of the fermenter 10 and the cessation of the fermentation or the death of micro-organisms (this allows preserving a liquid culture medium under the same physicochemical conditions). The fermenter 10, in addition to being very simple in design and very cost-effective compared to fermenters of the prior art according to the first category, is therefore very reliable and secure. It has the advantage of not requiring motorized systems, and overcoming a need for opening and closing means actuated from the outside and therefore for closing means. It avoids the need for human interventions and the risks of external contamination.

The fermenter 10 having this feature has the additional advantage of being able to operate even better with varying levels of liquid medium inside the container 11, without the need to provide for a low or a variable height of the inner tube 12 or to use motorized systems for stirring the liquid medium. This allows to open or close the fluid communication devices 16 at different levels depending on the height of the liquid medium in the volume supplied with gas.

Preferably, each fluid communication device 16 is autonomous and switches from one configuration to the other without external action and regardless of the configuration adopted by any other fluid communication device 16 of the fermenter 10. In other words, the fluid communication devices 16 which are located at different heights are independent of each other and are not connected together in this particular embodiment, nor controlled from outside the fermenter. This feature does in no way prevent from considering a variant wherein the closing elements 18 (which are described in detail below) of a single fluid communication device 16, located at the same height, move synchronously, in particular by being actuated by a spring and/or by being connected together.

According to an embodiment having the advantage of its great simplicity while having a high reliability and a good efficiency, each fluid communication device 16 comprises a plurality of openings 17 each crossing the thickness of the partition wall and a plurality of closing elements 18, wherein each closing element 18 equips a corresponding aperture 17 and switches between:

an open position, corresponding to the first configuration of the fluid communication device 16, wherein the closing element 18 opens the corresponding opening 17 and authorizes the fluid communication between the first and second volumes V1, V2 through the opening 17 to allow the liquid medium and the gas contained in the container 11 to circulate freely from one volume to the other through the opening 17, and a closed position corresponding to the second configuration of the fluid communication device 16, wherein the closing element 18 closes at least partially the corresponding opening 17 and blocks all or part of the fluid communication between the first and second volumes V1, V2 through the opening 17 for the liquid medium and the gas contained in the container 11.

In practice in the illustrated example, each opening 17 is a window 30 or a vent passing through the entire thickness of the inner tube 12, in the sense that this window opens into both the first volume V1 and the second volume V2. The contour of each opening 17 may be of any shape, for example of rectangular shape as shown. The openings 17 equipping each fluid communication device 16 may be of any number, for example equal to 4, as shown in the embodiment illustrated in the figures. For a given fluid communication device 16, the openings 17 equipping it are arranged at the same given height of the inner tube 12 and are angularly distributed about its axis of extension, at a regular pitch or not.

Figure 2:
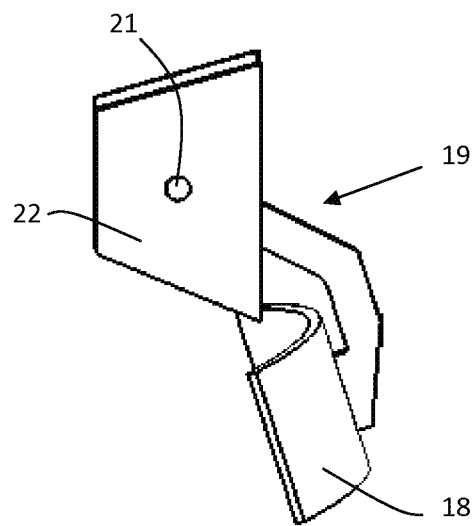
FIG. 2 is a perspective view of a closing element and of the corresponding connection mechanism used in the fermenter of FIG. 1.
Figure 3:
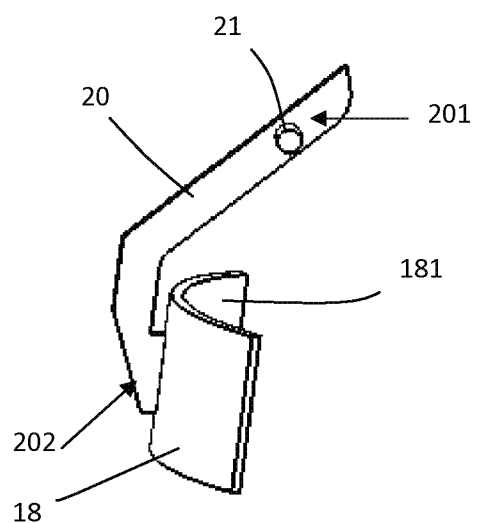
FIG. 3 is a perspective view of the closing element and of the support arm shown in FIG. 2.

With reference to FIGS. 2 and 3, each fluid communication device 16 may comprise, for each closing element 18, a corresponding connecting mechanism 19 allowing to fasten the closing element 18 on the partition wall movably between the closed and open positions. In the appended FIGS. 1, 4A and 4B, the open position is shown for all the fluid communication devices 16. In FIG. 6, the open position is shown for the upper fluid communication device 16 and the closed position is shown for the lower fluid communication device 16. In all the figures, the connecting mechanism 19 allows for example fastening the closing element 18 on the inner tube 12.

Each connecting mechanism 19 is configured such that the closing element 18 is mechanically placed automatically in its open position under the action of the difference between the pressure in the volume where the ascending circulation occurs and the pressure in the volume where the descending circulation occurs, when this difference takes a value greater than the predetermined threshold value already mentioned above.

Each connecting mechanism 19 is configured so that the closing element 18 is mechanically placed automatically in its closed position under the action of the difference between the pressure in the volume where the ascending circulation occurs and the pressure in the volume where the descending circulation occurs, when this difference takes a value less than or equal to the predetermined threshold value.

According to a simple, cost-effective, reliable and efficient embodiment, the connecting mechanism 19 associated with each closing element 18 comprises a hinge means of the closing element 18 relative to the partition wall about a pivot axis 21 located above the corresponding opening 17, the switching from the open position to the closed position and vice versa occurring by tilting the closing element 18 about this pivot axis 21. In practice in the illustrated example, the hinge means allows hinging the closing element 18 relative to the inner tube 12.

Preferably, the connecting mechanism 19 is such that the pivot axis 21 is permanently disposed in the volume where the ascending circulation occurs while the closing element 18 is permanently disposed (regardless of its position between its closed position and its open position) in the volume where the descending circulation occurs.

That is why, in the particular illustrated example of the fermenter 10, the pivot axis 21 is disposed in the first volume V1 wherein the ascending circulation of the mixture between the liquid medium and the injected gas occurs while the closing element 18 is permanently disposed, that is to say regardless of its position between its closed position and its open position, in the volume where the descending circulation occurs, which corresponds here to the second volume V2.

This arrangement has the advantage of reinforcing, under normal operating condition, the self-closing of each closing element 18 towards its closed position under the action of gravity, by positioning very advantageously the center of gravity of the connecting mechanism 19 in the volume (here the first volume V1) where the ascending circulation occurs.

Furthermore, for the same purpose, the connecting mechanism 19 associated with each closing element 18 may comprise a support arm 20 having a first end 201 hinged about the pivot axis 21 at the hinge means and a second end 202 connected to the closing element 18. The support arm 20 passes through the thickness of the partition wall, concretely through the thickness of the inner tube 12 in the illustrated example, for example in an area located above the opening 17 to be closed by the closing element 18 supported by this support arm 20. The support arm 20 may alternatively pass through the thickness of the partition wall through the opening 17. The pivot axis 21 may be or not secured to the support arm 20. The part constituting the pivot axis 21 can in particular be formed integrally with the rest of the support arm 20 at the first end 201.

These arrangements have the additional advantage of allowing a switching to the open position of the closing element 18 even in the case where the difference between the pressure of the volume where the ascending circulation occurs and the pressure of the volume where the descending circulation occurs is small. In other words, the sensitivity toward the second configuration of each device 16 is high and it can be obtained under the action of a small pressure difference between the ascending circulation volume and the descending circulation volume.

Each connecting mechanism 19 comprises for example a fixing clevis 22 on which the pivot axis 21 is hinged, which constitutes in practice the aforementioned hinge means, the fixing clevis 22 being fastened to the partition wall. In particular, the fixing clevis 22 is disposed continuously, that is to say regardless of the position occupied by the closing element 18 between its closed position and its open position, in the volume where the ascending circulation occurs, which corresponds to the first volume V1 in the illustrated example. The connection between the inner face of the inner tube 12 and the connecting clevis 22 may be of the embedding type, for example by gluing or welding, although any other type of mechanical connection may be considered, for example providing for the presence of at least one degree of freedom in translation and/or in rotation if necessary.

The predetermined threshold value can be determined by the shape of the support arm 20 and by the depth of the pivot axis 21 within the ascending circulation volume, determining a vacuum closing force, hence a minimum pressure difference allowing to open the closing element 18. The weight of the closing elements 18 and/or the length of the support arms 20 can also be taken into account in the predetermination of the opening/closing threshold.

The general functional principles of the invention having been presented in detail hereinabove, the Applicant presents hereinafter a detailed description of three exemplary embodiments of the fermenter 10 according to the invention, having respectively a useful volume of 3.75 L, 350 L and 840 L.

In the example of the fermenter 10 whose useful volume is 3.75 L, the total height of the first volume V1 where the ascending circulation occurs is equal to 476 mm while the inner diameter of the tube that delimits it is equal to 60 mm. The inner diameter of the tube that externally delimits the second volume V2 where the descending circulation occurs is for its part equal to 100 mm while its height is equal to 576 mm. There are two fluid circulation devices 16 offset from one another along the height of the fermenter 10, respectively located at 210 and 322 mm from the bottom of the second volume V2. Each of these two devices 16 comprises at least two openings 17 and two corresponding closing elements 18 located at the same height. More precisely, each opening 17 allows a fluid communication between the first volume V1 and the second volume V2 and has a rectangular contour of 14 mm over 36 mm. Each closing element 18, made of 1 mm stainless steel, conforms perfectly to the shape of the outer wall of the tube that delimits the first volume V1. The length of each closing element is 45 mm while its height is 20 mm. The pivot axis 21 of the arm 20 is offset inwardly of the first volume V1 relative to the wall of the tube that delimits the first volume V1 at a distance of 10.75 mm. The arm 20 has a length of 50 mm and has a maximum angular pivoting travel between its closed position (wherein the arm 20 is oriented vertically) and its open position equal to 61°. It is thus avoided that the closing member 18 rubs against the inner wall of the tube that delimits externally the second volume V2 and that it gets stuck thereon.

In the example of the fermenter 10 whose useful volume is 350 L, the total height of the first volume V1 where the ascending circulation occurs is equal to 3000 mm while the inner diameter of the tube that delimits it is equal to 219 mm. The inner diameter of the tube that externally delimits the second volume V2 where the descending circulation occurs is for its part equal to 400 mm while its height is equal to 4000 mm. There are provided three fluid circulation devices 16 offset from each other along the height of the fermenter 10, respectively located at 521 mm, 1354 mm and 2180 mm from the bottom of the second volume V2. Each of these three devices 16 comprises four openings 17 and four corresponding closing elements 18 located at the same height. More precisely, each opening 17 allows a fluid communication between the first volume V1 and the second volume V2 and has a rectangular contour of 123 mm to 68 mm. Each closing element 18, made of 1 mm stainless steel, perfectly conforms to the shape of the outer wall of the tube that delimits the first volume V1. The length of each closing element is 153 mm while its height is 93 mm. The pivot axis 21 of the arm 20 is offset inwardly of the first volume V1 relative to the wall of the tube that delimits the first volume V1 at a distance of 32 mm. The arm 20 has a length of 75 mm and has a maximum angular pivoting travel between its closed position (wherein the arm 20 is oriented vertically) and its open position equal to 61°. It is thus avoided that the closing element 18 rubs against the inner wall of the tube that externally delimits the second volume V2 and that it gets stuck thereon.

In the example of the fermenter 10 whose useful volume is 840 L, the total height of the first volume V1 where the ascending circulation occurs is equal to 3000 mm while the inner diameter of the tube that delimits it is equal to 419 mm. The inner diameter of the tube that externally delimits the second volume V2 where the descending circulation occurs is for its part equal to 600 mm while its height is equal to 4000 mm. There are provided four fluid circulation devices 16 offset from each other along the height of the fermenter 10, respectively located at 321 mm, 996 mm, 1671 mm and 2346 mm from the bottom of the second volume V2. Each of these four devices 16 comprises four openings 17 and four corresponding closing elements 18 located at the same height. More precisely, each opening 17 allows a fluid communication between the first volume V1 and the second volume V2 and has a rectangular contour of 230 mm to 68 mm. Each closing element 18, made of 1 mm stainless steel, perfectly conforms to the shape of the outer wall of the tube that delimits the first volume V1. The length of each closing element is 284 mm while its height is 93 mm. The pivot axis 21 of the arm 20 is offset inwardly of the first volume V1 relative to the wall of the tube that delimits the first volume V1 at a distance of 32 mm. The arm 20 has a length of 75 mm and has a maximum angular pivoting travel between its closed position (wherein the arm 20 is oriented vertically) and its open position equal to 61°. It is thus avoided that the closing element 18 rubs against the inner wall of the tube that externally delimits the second volume V2 and that it gets stuck thereon.

According to another alternative embodiment not shown, the connecting mechanism 19 associated with each closing element 18 comprises, on the one hand, a sliding means by translation of the closing element 18 relative to the partition wall along a substantially horizontal direction of translation, the switching from the open position to the closed position and vice versa occurring by sliding the closing member 18 along this direction of translation and, on the other hand, an elastic return member biasing the closing member 18 permanently towards its closed position and such that the switching to the open position occurs by opposing the biasing mechanical action of the elastic return member on the closing element 18.

In this alternative variant, the biasing mechanical action applied by the elastic return member is taken into account in the definition and the characterization of each predetermined threshold value beyond which the fluid communication device 16 switches to its first configuration and the closing member 18 switches to its open position.

In order to allow a good operating efficiency while preserving the simplicity and the cost-efficiency of the fermenter 10, the closing element 18 may comprise a bearing face 181 intended to bear against the partition wall, that is to say here against the inner tube 12, in its closed position and having a spatial shape complementary to the shape of the area of the partition wall at which this bearing face 181 comes into contact. This allows in particular ensuring a good efficiency of the closed position, at lower cost.

In the illustrated example of the fermenter 10, the outer face of the inner tube 12 is generally cylindrical and convex with a circular section, such that the bearing face 181 is a concave surface in a cylindrical portion of complementary shape.

In the foregoing, each closing element 18 may however be of any nature in terms of shape as well as structure or hardness. In the illustrated example, the closing element 18 is rigid and takes the shape of a simple closure flap, but this is not restrictive.

Although the embodiment previously described for the fermenter 10 has numerous advantages and is particularly effective, alternative solutions can be considered for the design of said at least one fluid communication device 16.

Constituting the partition wall in the shape of an inner tube 12 is in no way restrictive. In addition, it is for example possible to provide for flexible flaps without hinge means or closing elements partially closing the opening. It is also possible to provide for a mechanization, for example using cylinders, and with detection by sensors. It is also possible to form all the closing elements of a fluid communication device 16 in a single tube rotating inside or outside the inner tube 12 and exposing the openings 17 of this device 16 via the rotation of the second tube. An alternative solution consists in providing that the tube attached to the inside or to the outside of the inner tube 12 is slidable in the inner tube along its height depending on the level.

An additional advantage of the fermenter 10 according to the invention is being adaptable to already existing "air lift"-type fermenters.

On the other hand, the fermenter 10 previously described has the advantage of not using flotation elements which would otherwise partially obstruct the ascending or descending circulation volume and thereby disrupt the circulation of the fluids vertically: the result is the guarantee of a good fluid and homogeneous circulation within the fermenter 10.

Finally, the automatic opening and the automatic closing of the fluid communication devices 16 allow working so as to use, regardless of the height of the liquid medium, the maximum circulation height of the liquid medium: in case of a drop in the level of the liquid medium in the fermenter 10 then causing a reversal of the pressure differential between the ascending and descending circulation volumes, the device(s) 16, located just below the level of the liquid medium open(s), allowing the circulation of fluids to continue between the two volumes. However, the devices 16 located at a still low level remain closed. If the level of liquid medium drops further below this or these open devices, it is the one or those still located below that will open, but not those located at a height lower than those that have just opened and so on. Thus, the maximum height is maintained for the ascending and descending circulations regardless of the level of the liquid medium in the fermenter 10, thus a better stirring and an optimization of the gas exchanges. Otherwise, in case of a rise in the level of liquid medium, the process works upside down in the same way.

The invention claimed is:

1. A fermenter for a liquid medium, comprising:
 a container adapted to contain the liquid medium, a partition wall positioned in the container and separating first and second volumes, an injecting device for injecting gas into a lower part of one of the first or second volumes in order to create in the one of the first or second volumes an ascending circulation of a mixture between the liquid medium and the injected gas and a descending circulation of a mixture in the one of the first or second volumes not supplied with gas by the injection device, wherein the partition wall is equipped with at least one fluid communication device for establishing a fluid communication between the first and second volumes configured to automatically switch between:
 a first configuration wherein the at least one fluid communication device allows, for the liquid medium and the gas contained in the container, a free fluid circulation from one of the first or second volumes to the other one of the first or second volumes through the at least one fluid communication device, the first configuration being assumed as soon as, at the at least one fluid communication device, the difference between the pressure of the mixture in the one of the first or second volumes where the ascending circulation occurs and the pressure of the mixture in the one of the first or second volumes where the descending circulation occurs is greater than a predetermined threshold value,
 and a second configuration wherein the at least one fluid communication device blocks all or part of the fluid circulation for the liquid medium and the gas contained in the container, the second configuration being assumed as soon as, at the at least one fluid communication device, the difference between the pressure of the mixture in the one of the first or second volumes where the ascending circulation occurs and the pressure of the mixture in the one of the first or second volumes where the descending circulation occurs is less than or equal to the predetermined threshold value, wherein the at least one fluid communication device is autonomous and switches from one configuration to the other without external action and regardless of the configuration adopted by any other fluid communication device of the fermenter.

2. The fermenter according to claim 1, wherein the at least one communication device is a plurality of separate fluid communication devices arranged in different areas of the partition wall which are staggered along a height of the partition wall.

3. The fermenter according to claim 1, wherein the at least one fluid communication device comprises a plurality of openings crossing a thickness of the partition wall and a plurality of closing elements, wherein each closing element of the plurality of closing elements equips a corresponding opening and switches between:
 an open position, corresponding to the first configuration of the ay least one fluid communication device, wherein each closing element of the plurality of closing elements opens the corresponding opening and authorizes the at least one fluid communication between the first and second volumes through the opening to allow the liquid medium and the gas contained in the container to circulate freely from one volume of the first or second volumes to another one of the first or second volumes through the opening,
 and a closed position, corresponding to the second configuration of the at least one fluid communication device, wherein each closing element of the plurality of closing elements closes at least partially the corresponding opening and blocks all or part of the at least one fluid communication between the first and second volumes through the opening for the liquid medium and the gas contained in the container.

4. The fermenter according to claim 3, wherein the at least one fluid communication device comprises, for each closing element of the plurality of closing elements, a corresponding connecting mechanism allowing to fasten the closing element on the partition wall movably between the closed and open positions.

5. The fermenter according to claim 4, wherein each connecting mechanism is configured such that the closing element corresponding thereto is mechanically placed automatically in its open position under the action of the difference between the pressure of the mixture in the one of the first or second volumes where the ascending circulation occurs and the pressure of the mixture in the one of the first or second volumes where the descending circulation occurs when this difference takes a value greater than the predetermined threshold value.

6. The fermenter according to claim 4, wherein each connecting mechanism is configured such that the closing element corresponding thereto is mechanically placed automatically in its closed position under the action of the difference between the pressure of the mixture in the one of the first or second volumes where the ascending circulation occurs and the pressure of the mixture in the one of the first or second volumes where the descending circulation occurs when this difference takes a value less than or equal to the predetermined threshold value.

7. The fermenter according to claim 4, wherein each closing element of the plurality of closing elements is hinged relative to the partition wall about a pivot axis located above the corresponding opening, the switching from the open position to the closed position and vice versa occurring by tilting the closing element about the pivot axis.

8. The fermenter according to claim 7, wherein the each connecting mechanism is such that the pivot axis corresponding thereto is disposed in the one of the first or second volumes where the ascending circulation occurs and in that the closing element corresponding thereto is disposed in the one of the first or second volumes where the descending circulation occurs.

9. The fermenter according to claim 7, wherein the connecting mechanism associated with each closing element of the plurality of closing elements comprises a support arm having a first end hinged about the pivot axis corresponding thereto and a second end connected to the closing element, the support arm passing through the thickness of the partition wall.

10. The fermenter according to claim 7, wherein a center of gravity of each connecting mechanism is located in the one of the first or second volumes where the ascending circulation occurs.

11. The fermenter according to claim 3, wherein each closing element of the plurality of closing elements comprises a bearing face intended to bear against the partition wall in the closed position of the closing element and having a spatial shape complementary to a shape of an area of the partition wall at which the bearing face comes into contact.

12. The fermenter according to claim 1, wherein the partition wall is formed in an inner tube positioned in the container such that the inner tube internally delimits the first volume and externally delimits the second volume in combination with the container.

13. The fermenter according to claim 1, wherein the at least one fluid communication device is automatic in a manner requiring no manual intervention.

14. A fermenter for a liquid medium, comprising:
a container adapted to contain the liquid medium, a partition wall positioned in the container and separating first and second volumes, an injecting device for injecting gas into a lower part of one of the first or second volumes in order to create in the one of the first or second volumes an ascending circulation of a mixture between the liquid medium and the injected gas and a descending circulation of a mixture in the one of the first or second volumes not supplied with gas by the injection device, wherein the partition wall is equipped with at least one fluid communication device for establishing a fluid communication between the first and second volumes configured to automatically switch between:
a first configuration wherein the at least one fluid communication device allows, for the liquid medium and the gas contained in the container, a free fluid circulation from one of the first or second volumes to the other one of the first or second volumes through the at least one fluid communication device, the first configuration being assumed as soon as, at the at least one fluid communication device, the difference between the pressure of the mixture in the one of the first or second volumes where the ascending circulation occurs and the pressure of the mixture in the one of the first or second volumes where the descending circulation occurs is greater than a predetermined threshold value,
and a second configuration wherein the at least one fluid communication device blocks all or part of the fluid circulation for the liquid medium and the gas contained in the container, the second configuration being assumed as soon as, at the at least one fluid communication device, the difference between the pressure of the mixture in the one of the first or second volumes where the ascending circulation occurs and the pressure of the mixture in the one of the first or second volumes where the descending circulation occurs is less than or equal to the predetermined threshold value,
wherein the at least one fluid communication device comprises a plurality of openings crossing a thickness of the partition wall and a plurality of closing elements, wherein each closing element of the plurality of closing elements equips a corresponding opening and switches between:
an open position, corresponding to the first configuration of the fluid communication device, wherein each closing element of the plurality of closing elements opens the corresponding opening and authorizes the at least one fluid communication between the first and second volumes through the opening to allow the liquid medium and the gas contained in the container to circulate freely from one volume of the first or second volumes to another one of the first or second volumes through the opening,
and a closed position, corresponding to the second configuration of the at least one fluid communication device, wherein each closing element of the plurality of closing elements closes at least partially the corresponding opening and blocks all or part of the at least one fluid communication between the first and second volumes through the opening for the liquid medium and the gas contained in the container,
wherein the at least one fluid communication device comprises, for each closing element of the plurality of closing elements, a corresponding connecting mechanism allowing to fasten the closing element on the partition wall movably between the closed and open positions, and
wherein each connecting mechanism is configured such that the closing element corresponding thereto is mechanically placed automatically in its open position under the action of the difference between the pressure of the mixture in the one of the first or second volumes where the ascending circulation occurs and the pressure of the mixture in the one of the first or second volumes where the descending circulation occurs when this difference takes a value greater than the predetermined threshold value.

15. The fermenter according to claim 14, wherein the at least one fluid communication device is a plurality of separate fluid communication devices arranged in different areas of the partition wall which are staggered along a height of the partition wall.

16. The fermenter according to claim 14, wherein the at least one fluid communication device is autonomous and switches from one configuration to the other without external action and regardless of the configuration adopted by any other fluid communication device of the fermenter.

17. The fermenter according to claim 14, wherein each connecting mechanism is configured such that the closing element corresponding thereto is mechanically placed automatically in its closed position under the action of the difference between the pressure of the mixture in the one of the first or second volumes where the ascending circulation occurs and the pressure of the mixture in the one of the first or second volumes where the descending circulation occurs when this difference takes a value less than or equal to the predetermined threshold value.

18. The fermenter according to claim 14, wherein each closing element of the plurality of closing elements is hinged relative to the partition wall about a pivot axis located above the corresponding opening, the switching from the open position to the closed position and vice versa occurring by tilting the closing element about the pivot axis.

19. The fermenter according to claim 18, wherein each connecting mechanism is such that the pivot axis corresponding thereto is disposed in the one of the first or second volumes where the ascending circulation occurs and in that the closing element corresponding thereto is disposed in the one of the first or second volumes where the descending circulation occurs.

20. The fermenter according to claim 18, wherein the connecting mechanism associated with each closing element of the plurality of closing elements comprises a support arm having a first end hinged about the pivot axis corresponding thereto and a second end connected to the closing element, the support arm passing through the thickness of the partition wall.

21. The fermenter according to claim 18, wherein a center of gravity of each connecting mechanism is located in the one of the first or second volumes where the ascending circulation occurs.

22. The fermenter according to claim 14, wherein each closing element of the plurality of closing elements comprises a bearing face intended to bear against the partition wall in the closed position of the closing element and having a spatial shape complementary to a shape of an area of the partition wall at which the bearing face comes into contact.

23. The fermenter according to claim 14, wherein the partition wall is formed in an inner tube positioned in the container such that the inner tube internally delimits the first volume and externally delimits the second volume in combination with the container.

24. The fermenter according to claim 14, wherein the at least one fluid communication device is automatic in a manner requiring no manual intervention.

25. A fermenter for a liquid medium, comprising:
a container adapted to contain the liquid medium, a partition wall positioned in the container and separating first and second volumes, an injecting device for injecting gas into a lower part of one of the first or second volumes in order to create in the one of the first or second volumes an ascending circulation of a mixture between the liquid medium and the injected gas and a descending circulation of a mixture in the one of the first or second volumes not supplied with gas by the injection device, wherein the partition wall is equipped with at least one fluid communication device for establishing a fluid communication between the first and second volumes configured to automatically switch between:
a first configuration wherein the at least one fluid communication device allows, for the liquid medium and the gas contained in the container, a free fluid circulation from one of the first or second volumes to the other one of the first or second volumes through the at least one fluid communication device, the first configuration being assumed as soon as, at the at least one fluid communication device, the difference between the pressure of the mixture in the one of the first or second volumes where the ascending circulation occurs and the pressure of the mixture in the one of the first or second volumes where the descending circulation occurs is greater than a predetermined threshold value,
and a second configuration wherein the at least one fluid communication device blocks all or part of the fluid circulation for the liquid medium and the gas contained in the container, the second configuration being assumed as soon as, at the at least one fluid communication device, the difference between the pressure of the mixture in the one of the first or second volumes where the ascending circulation occurs and the pressure of the mixture in the one of the first or second volumes where the descending circulation occurs is less than or equal to the predetermined threshold value,
wherein the at least one fluid communication device comprises a plurality of openings crossing a thickness of the partition wall and a plurality of closing elements, wherein each closing element of the plurality of closing elements equips a corresponding opening and switches between:
an open position, corresponding to the first configuration of the at least one fluid communication device, wherein each closing element of the plurality of closing elements opens the corresponding opening and authorizes the at least one fluid communication between the first and second volumes through the opening to allow the liquid medium and the gas contained in the container to circulate freely from one volume of the first or second volumes to another one of the first or second volumes through the opening,
and a closed position, corresponding to the second configuration of the at least one fluid communication device, wherein each closing element of the plurality of closing elements closes at least partially the corresponding opening and blocks all or part of the at least one fluid communication between the first and second volumes through the opening for the liquid medium and the gas contained in the container,
wherein the at least one fluid communication device comprises, for each closing element of the plurality of closing elements, a corresponding connecting mechanism allowing to fasten the closing element on the partition wall movably between the closed and open positions,
wherein each closing element of the plurality of closing elements is hinged relative to the partition wall about a pivot axis located above the corresponding opening, the switching from the open position to the closed position and vice versa occurring by tilting the closing element about the pivot axis, and
wherein each connecting mechanism is such that the pivot axis corresponding thereto is disposed in the one of the first or second volumes where the ascending circulation occurs and in that the closing element corresponding thereto is disposed in the one of the first or second volumes where the descending circulation occurs.

26. The fermenter according to claim 25, wherein the at least one fluid communication device is a plurality of separate fluid communication devices arranged in different areas of the partition wall which are staggered along a height of the partition wall.

27. The fermenter according to claim 25, wherein the at least one fluid communication device is autonomous and switches from one configuration to the other without external action and regardless of the configuration adopted by any other fluid communication device of the fermenter.

28. The fermenter according to claim 25, wherein each connecting mechanism is configured such that the closing element corresponding thereto is mechanically placed automatically in its open position under the action of the difference between the pressure of the mixture in the one of the first or second volumes where the ascending circulation occurs and the pressure of the mixture in the one of the first or second volumes where the descending circulation occurs when this difference takes a value greater than the predetermined threshold value.

29. The fermenter according to claim 25, wherein each connecting mechanism is configured such that the closing element corresponding thereto is mechanically placed automatically in its closed position under the action of the difference between the pressure of the mixture in the one of the first or second volumes where the ascending circulation occurs and the pressure of the mixture in the one of the first or second volumes where the descending circulation occurs when this difference takes a value less than or equal to the predetermined threshold value.

30. The fermenter according to claim 25, wherein the connecting mechanism associated with each closing element of the plurality of closing elements comprises a support arm having a first end hinged about the pivot axis corresponding thereto and a second end connected to the closing element, the support arm passing through the thickness of the partition wall.

31. The fermenter according to claim 25, wherein a center of gravity of each connecting mechanism is located in the one of the first or second volumes where the ascending circulation occurs.

32. The fermenter according to claim 25, wherein each closing element of the plurality of closing elements comprises a bearing face intended to bear against the partition wall in the closed position of the closing element and having a spatial shape complementary to a shape of an area of the partition wall at which the bearing face comes into contact.

33. The fermenter according to claim 25, wherein the partition wall is formed in an inner tube positioned in the container such that the inner tube internally delimits the first volume and externally delimits the second volume in combination with the container.

34. The fermenter according to claim 25, wherein the at least one fluid communication device is automatic in a manner requiring no manual intervention.

* * * * *